United States Patent [19]
Reed et al.

[11] Patent Number: 5,258,825
[45] Date of Patent: Nov. 2, 1993

[54] OPTICAL COMPOSITIONAL ANALYZER APPARATUS AND METHOD FOR DETECTION OF ASH IN WHEAT AND MILLED WHEAT PRODUCTS

[75] Inventors: David S. Reed, Truckee, Calif.; James J. Psotka, Reno, Nev.

[73] Assignee: Perten Instruments North America, Inc., Reno, Nev.

[21] Appl. No.: 791,884

[22] Filed: Nov. 13, 1991

[51] Int. Cl.⁵ .................................... G01N 21/25
[52] U.S. Cl. ............................ 356/402; 356/51; 356/419; 250/339; 250/341
[58] Field of Search ............. 356/39, 40, 41, 51, 356/402, 407, 414, 416, 419, 420; 250/339, 338.5, 341

[56] References Cited

U.S. PATENT DOCUMENTS

| | | | |
|---|---|---|---|
| 3,647,299 | 3/1972 | Lavallee | 356/41 |
| 3,828,173 | 8/1974 | Knepler | . |
| 3,861,788 | 1/1975 | Webster | . |
| 4,037,970 | 7/1977 | Webster | . |
| 4,082,464 | 4/1978 | Johnson, Jr. | . |
| 4,167,331 | 9/1979 | Nielsen | 356/39 |
| 4,236,076 | 11/1980 | Judge et al. | 250/347 |
| 4,260,262 | 4/1981 | Webster | 356/418 |
| 4,404,642 | 9/1983 | Rosenthal | 364/498 |
| 4,443,108 | 4/1984 | Webster | 356/418 |
| 4,627,008 | 12/1986 | Rosenthal | 364/498 |
| 4,883,963 | 11/1989 | Kemeny et al. | 250/339 |

OTHER PUBLICATIONS

"Near-Infrared Reflectance Analysis" D. L. Wetzel, Analytical Chemistry, vol. 55, p1 1165A (1983).

*Primary Examiner*—F. L. Evans
*Attorney, Agent, or Firm*—Flehr, Hohbach, Test, Albritton & Herbert

[57] ABSTRACT

An optical analyzing apparatus (20) for obtaining a quantitative correlation spectroscopy measurements of an analyte concentration in a multiple constituent sample (24). The optical analyzing apparatus (20) employs a correlation spectroscopy algorithm which uses preselected wavelength light energy from both the visible light spectrum and the near-infrared (NIR) light spectrum to analyze multiconstituent samples. The optical analyzing apparatus (20) comprises a light emitter mechanism (22) formed for irradiating the sample (24) with a predetermined first wavelength of light energy in the visible light spectrum and a predetermined second wavelength of light energy in the NIR spectrum. The first wavelength is selected to be active in response to the presence of the analyte while the second wavelength is selected to be active in response to the presence of at least one of the remaining constituents in the sample (24). A detector mechanism (50) is positioned to detect one of optical reflectance and transmissivity of the sample (24) after irradiation at the first and second wavelength, whereby the detected one of reflectance and transmissivity can be used in correlation spectroscopy algorithms to obtain a value of the concentration.

30 Claims, 2 Drawing Sheets

OPTICAL COMPOSITIONAL ANALYZER APPARATUS AND METHOD FOR DETECTION OF ASH IN WHEAT AND MILLED WHEAT PRODUCTS

BACKGROUND OF THE INVENTION

1. Field of the Invention

The present invention relates, generally, to optical analyzing instruments and, more particularly, to optical analyzing instruments performing near infrared quantitative analysis.

2. Description of the Related Art

The percentage concentration of grain or milled grain constituents partially determines its economic or market value. Often, the value of the grain may depend upon its protein, oil and moisture concentration, or combination thereof. This may hold particularly true during the milling process of wheat where it is desirable to remove the outer portion of the kernel (sometimes referred to as "bran" or "flour ash") from the milled flour. Improperly milled flour may be very wasteful, time inefficient and, further, increase milling cost if not corrected within a reasonable time frame.

Traditionally, chromatographic methods or indirect separation chemical analysis were employed as the only accurate constituent analysis techniques. The individual constituents were chemically separated from the specimen and analyzed for percentage concentration. For example, the Kjeldahl technique is a traditional analytical laboratory technique used to determine the protein content. Techniques such as these, although highly accurate, are relatively time consuming and generally require skilled chemists to conduct most technical operations. Typically, at least four hours are necessary to perform this analysis. Accordingly, it could be at least four hours before improperly milled flour is even discovered.

In the mid-sixties, Karl H. Norris of the USDA, observed that the absorbtivity, as determined by transmissivity or reflectivity, of near-infrared (NIR) light energy incident on a specimen surface is proportional to its composition and constituent concentrations. That is, quantitative diffuse reflectance in the near-infrared region is a function of the percentage of an analyte's concentration. Therefore, because particular grain constituents actively respond to at least one particular NIR light energy wavelength, by applying correlation spectroscopy the constituent concentration may be determined.

Typically, to analyze a grain specimen using NIR correlation spectroscopy, the sample is irradiated with preselected filtered light energy as it passes from a source, generally a wide band wavelength quartz tungsten-halogen light source or a narrow band Near-Infrared Emitting Diodes (NIREDs), to irradiate the sample. Currently, two types of NIR quantitative analysis instruments are commercially available. One type measures the sample diffuse reflectance while the other measures the sample transmissivity. In either type, the reflectivity or transmissivity of the preselected wavelength light incident on the sample, as set forth above, is a function of its constituent concentration.

It is well known that the analyte concentration is functionally proportional to the spectroscopic response by dither individual wavelengths, by difference between pairs of wavelengths, and by trios, where the reflectance of the central wavelength is mathematically weighted in comparison to the contribution of reflectance at wavelengths incrementally spaced on either side. Typical of such an individual wavelength algorithm is set forth below:

$$\%_{Const} = a_0 + a_1 \log(1/R_1) + a_2 \log(1/R_2) + \ldots + a_n \log(1/R_n)$$

where $a_0$ = calibration offset, $a_{1,2,\ldots n}$ = are calculated calibration coefficients, and $R_{1,2,\ldots n} = (I_n/I_r)$, i.e., the intensity of the preselected reflected from a sample light as compared to the intensity of the preselected reflected light from a reference.

Moreover, simultaneous multicomponent analysis is possible through the solution of multiple equations, such as:

$$\%_{Oil} = a_0 + a_1 \log(1/R_0) + a_2 \log(1/R_w) + a_3 \log(1/R_p);$$

$$\%_{Water} = a_4 + a_5 \log(1/R_0) + a_6 \log(1/R_w) + a_7 \log(1/R_p);$$

$$\%_{Protein} = a_7 + a_8 \log(1/R_0) + a_9 \log(1/R_w) + a_{10} \log(1/R_p),$$

for example. Through these selected correlation spectroscopy algorithms and corresponding calibration offsets and coefficients, the particular constituent concentrations can be predicted from the diffuse reflectance intensities measured at different wavelengths. This technique is set forth and better detailed in the article entitled "Near-Infrared Reflectance Analysis" by D.L. Wetzel, Analytical Chemistry, Vol. 55, p. 1165A (1983).

Typically, a quartz tungsten-halogen light source emitting a wide band of wavelengths is used to irradiate the specimen through discrete selected wavelength interference filters mounted to a rotatable turret. These turrets include a plurality of radially positioned filters, each of which is designed to pass light at a preselected wavelength which are known to be optically reactive in determining the percentage concentration of the measured constituents.

In a limited capacity, computational circuitry, coupled to stored sensor signals and precalculated coefficients, have permitted this analysis technique to be commercially feasible. The agricultural community has increasingly relied on quantitative optical analyzers to determine moisture, starch, protein and oil, for example, in grain products. Typical of these devices are the perpendicularly impinging light sources described in U.S. Pat. Nos. 3,828,173, 4,236,076, 4,286,327 and 4,404,642, and the tilting interference filter systems set forth in U.S. Pat. Nos. 3,861,788 and 4,082,464.

These above-mentioned systems have often proved effective in determining certain grain constituent concentrations in milled and non-milled grains, such as protein, starch and moisture. One problem, however, is that these techniques are difficult to apply when the variety of wheat flour changes. Thus, each variety has heretofore required time-consuming recalibration of the equipment.

Mineral ash of a flour sample is directly proportional to the amount of bran layer of a wheat kernel that is left in the flour after the milling process. Thus, "ash" concentration determination is an important indicator of the undesirable residual mineral content not removed during milling.

Although it is possible through NIR optical analysis to predict concentrations of flour "ash" in milled wheat grain, the traditional preselected NIR wavelengths in the range of 1445 nm to 2348 nm have not yielded consistent results, particularly as the wheat variety changes. Commercial NIR instrumentation for flour ash usually employ standard combinations of interference filters, such as 1680 nm in combination with 2336 nm. Through correlation spectroscopy, these optical analyzers have been sufficient when calibrated for a particular blend of wheat flour. However, these instruments have been unreliable for predicting "ash" when applied to a wide variety of wheat flour. To obtain acceptable accuracy, recalibration (i.e., new set of calibration offsets and/or coefficients) is often necessary for each separate wheat flour blend. Therefore, the prior art quantitative optical analyzers have been extremely sensitive to matrix changes when quantifying flour "ash".

Ultimately, this recalibration problem is too burdensome for commercial feasibility. The flour grade is continually changing during the milling process. By the time a proper set of calibration offsets and coefficients are determined, that particular blend of wheat flour may be finished being milled and a new, slightly differing blend of wheat flour introduced.

Moreover, typical NIR optical analysis for wheat flour "ash" have been too sensitive to particle size variations. Unless the particle size difference from sample to sample is minimized, the optical analysis could not be accurately relied upon, even when using the proper calibration coefficients. Unfortunately, different wheat flour blends often differ in particle size. Although uniform particle size in milled flour is desirable, in order for these analyzers to function properly and accurately, it is often not practical.

Other optical techniques are sometimes employed to determine the flour "ash" concentration. For example, "ash" concentration in flour is sometimes estimated by the flour coloration alone. The brownish color of bran actively responds to the visible light range between 540 nm to 560 nm. Incidentally, this corresponds to the green to yellow color cross-over in the visible light spectrum. The basic premise is that wheat bran concentration in wheat flour discolors the wheat flour so that visual changes in the color can be detected. Thus, by measuring the tone or "color" of the flour, the mineral "ash" concentration may be estimated through a "color" correlation algorithm, similar to the constituent correlation algorithm used in NIR spectroscopy.

Unfortunately, these color correlation measurements also result in unreliable predictions when employed in attempting to analyze changing wheat flour blends. Because of the slightly different wheat kernel colors, recalibration is often necessary for each blend if accurate predictions are desired. Moreover, any other impurities which discolor the wheat flour may be construed as "ash" impurities. Thus, the measurements may falsely represent the flour "ash" concentration and lead to incorrect estimations. These techniques are not practical for commercial usage where analytical accuracy is compromised for practicality.

Accordingly, it is an object of the present invention to provide an optical analyzing apparatus and method which more accurately determines the chemical constituent concentrations of a specimen.

It is another object of the present invention to provide an optical analyzing apparatus and method which more precisely and accurately determines the flour "ash" for a wider variety of milled wheat flour.

Still another object of the present invention is to provide an optical analyzing apparatus and method which is analytically applicable to a wider range of sample particle sizes.

Yet another object of the present invention to provide an optical analyzing apparatus and method which can be accurately and efficiently be employed during the milling process.

It is a further object of the present invention to provide an optical analyzing apparatus and method which is durable, compact, easy to maintain, has a minimum number of components, is easy to use by unskilled personnel, and is economical to manufacture.

The apparatus and method of the present invention has other objects and features of advantage which will be more readily apparent from the following description of the Best Mode of Carrying Out the Invention and the appended claims, when taken in conjunction with the accompanying drawing.

SUMMARY OF THE INVENTION

The present invention includes an optical analyzing apparatus for obtaining quantitative correlation spectroscopy measurements of an analyte concentration in a multiple constituent sample. Briefly, the optical analyzing apparatus of the present invention comprises a light emitter mechanism formed for irradiating the sample with a predetermined first wavelength of light energy in the visible light spectrum. This predetermined wavelength is selected to be active in response to the presence of the analyte. Further, a predetermined second wavelength of light energy in the near-infrared (NIR) spectrum is selected to be active in response to the presence of at least one of the remaining constituents in the sample. A detector mechanism is positioned to detect one of optical reflectance and transmissivity of the sample after irradiation at the first and second wavelength, whereby the detected one of reflectance and transmissivity can be used in correlation spectroscopy algorithms to obtain a value of the concentration.

In another aspect of the present invention, a method is provided for optically obtaining a quantitative measurement of an analyte concentration in a multiple constituent sample. Briefly, the method comprises the steps of irradiating the sample with a predetermined first wavelength of light energy in the visible light spectrum selected to be active in response to the presence of said analyte and detecting one of a first optical reflectance and transmissivity of the sample after the irradiation at the first wavelength. Furthermore, the method includes irradiating the sample with a predetermined second wavelength of light energy in the near-infrared (NIR) spectrum selected to be active in response to the presence of at least one of the remaining constituents in the sample and detecting one of a second optical reflectance and transmissivity of the sample after the irradiation at the second wavelength. The next step includes calculating a value of said concentration from said first and said second detected one of reflectance and transmissivity of the sample.

These and other features and advantages of the present invention will become more apparent from the following description of exemplary embodiment thereof, as illustrated in the accompanying drawing.

THE BEST MODE FOR CARRYING OUT THE INVENTION

The optical analyzing apparatus of the present invention employs a correlation spectroscopy algorithm in which a novel combination of preselected wavelengths of light energy, from both the visible light spectrum and the near-infrared (NIR) light spectrum, are used to analyze multiconstituent samples. The following description is presented to enable a person skilled in the art to make and use the invention, and is provided in the context of a particular application and its requirements. Various modifications to the preferred embodiment will be readily apparent to those skilled in the art, and the generic principles defined herein may be applied to other embodiments and applications without departing from the spirit and scope of the invention. Thus, the present invention is not intended to be limited to the embodiment shown, but is to be accorded with the widest scope consistent with the principles and features disclosed herein.

Figure 1:
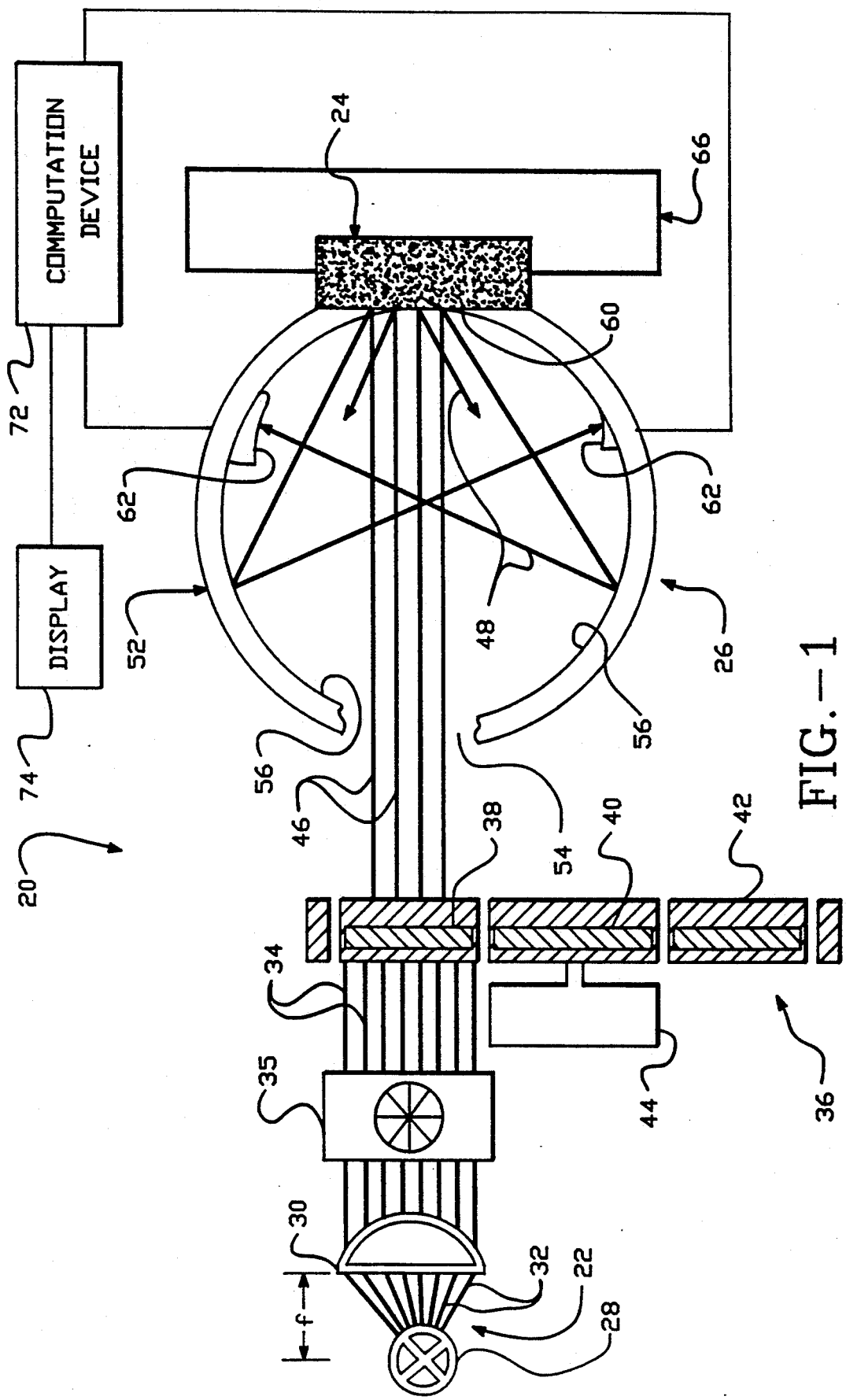
FIG. 1 is a schematical representation of the optical analyzing apparatus constructed in accordance with the present invention.

Attention is now directed to FIG. 1, where the subject optical analyzing apparatus, generally designated 20, is illustrated. In accordance with the present invention, apparatus 20, briefly, comprises a light emitter assembly, generally designated 22, formed for irradiating a sample 24 with a first and a second predetermined wavelength of light energy. In addition, a detector mechanism, generally designated 26, is positioned to detect one of optical reflectance and transmissivity of the sample after irradiation, whereby the detected one of reflectance and transmissivity can be used to predict, through a correlation spectroscopy algorithm, a value of the constituent or constituents concentration.

As is apparent from the present commercially available quantitative optical analyzers, the constituent concentrations of most samples are determined by irradiating the samples with NIR light energy. Typical optical analyzers, such as those employing individual or sequential combination of standard interference filters or near-infrared emitting diodes (NIREDs), as well as wavelength scanning or monochromatic devices, irradiate samples with light corresponding to the 1400 nm to 2500 nm NIR spectrum. In a practical sense, the basis of the success in using the NIR spectrum is that the wavelength reproducibility is measurably high. This is extremely important in correlation spectroscopy because the differences in measurements between two samples may be measured in Milliabsorbance units (i.e., log $(1/R) \times 10_3$). Generally speaking, when wavelength reproducibility is high, signals maximized, and noise minimized, then the optical responses are sensitive to the environment of the absorbing molecules and the number of the molecules present. Therefore, quantitative measurement can be made and successfully correlated to chemical data obtained through other methods. From this data and through the application of a suitable statistical relationship with appropriate calibration offsets and coefficients, determination of analyte concentrations of a sample can be accurately predicted.

The current quantitative correlation spectroscopic instruments rarely venture beyond the broad NIR spectrum. Generally, visible or ultraviolet "light" measurements do not provide adequate wavelength reproducibility nor adequate resolution of chemical peaks which are attainable in the NIR regions. In the mid-infrared spectrum, molecular absorptions are generally much higher and interferences are magnified to such a degree that separation therefrom becomes increasingly difficult. Thus, constituent concentration algorithms, employing one of the diffuse reflectance or transmissivity measurements in the NIR spectra in combination with the corresponding calibration offsets and coefficients, are currently believed to yield the best, most accurate constituent concentration analysis for a wide variety of applications. This is particularly true when determining wheat flour "ash" concentration.

Furthermore, as mentioned, visible color correlation is sometimes used to estimate the "ash" impurity of wheat flour strictly by the color of the flour. Any additional impurities which further discolor the wheat flour may be construed as "ash" impurities. Thus, these "color" measurements may falsely represent flour "ash" and lead to incorrect estimations. Typically, each variety wheat flour, of which there are many, requires an instrument recalibration (i.e., new set of calibration coefficients) in order to yield accurate results.

In accordance with the present invention, optical analyzing apparatus 20 applies a correlation spectroscopy algorithm which incorporates preselected wavelength light energy from both the visible light spectrum and the near-infrared (NIR) light spectrum to analyze multiconstituent samples. Apparatus 20 sequentially irradiates, in any order or combination thereof, sample 24 with radiant energy from both the NIR light spectrum and visible light spectrum. However, in contrast to the prior quantitative optical analyzing instruments, the present invention directly correlates the visible light measurement into the constituent correlation spectroscopy algorithm rather than applying this measurement to a "color" correlation determination. More specifically, rather than correlating a visible light measurement to "color" to estimate the constituent concentration, the visible light measurement is correlated directly to that particular constituent. The prior systems utilized visible light or a combination of visible light and NIR light energy for only "color" correlation measurements.

The application of an individual or plurality of visible light measurements together with an individual or plurality of NIR measurements at selected wavelengths, in an appropriate correlation spectroscopic algorithm, as will be discussed below, have led to astounding results. While retaining the accuracy of the prior instruments, which need to be recalibrated for each particular wheat flour blend or variety, the present invention has shown much less sensitivity to matrix changes. Accordingly, the present invention is much more applicable to a wider variety of blends without the need to continually recalibrate the optical analyzer for each particular wheat flour blend.

For example, TABLE 1 compares the "ash" concentration determined by the present invention with the "oven" method laboratory determination in eight typical varieties of wheat flour. As shown, these typical results illustrate the substantial flexibility and precision of the present invention when applied to a wide variety of flour samples.

TABLE 1

| Sample | Predicted "Ash" | Oven Method "Ash" |
| --- | --- | --- |
| #1 | 0.430% | 0.444% |
| #2 | 0.454% | 0.460% |

TABLE 1-continued

| Sample | Predicted "Ash" | Oven Method "Ash" |
|---|---|---|
| #3 | 0.461% | 0.459% |
| #4 | 0.462% | 0.463% |
| #5 | 0.464% | 0.472% |
| #6 | 0.474% | 0.476% |
| #7 | 0.500% | 0.493% |
| #8 | 0.510% | 0.505% |

One reason for the advantages of present invention, it is hypothesized, is that this visible light measurement corresponds to the optically active brownish color of bran. Accordingly, the analyte of bran is substantially absorbing light energy in this visible light spectrum as compared to the NIR spectrum. This is particularly important because the surface backscattering, after irradiation with sample 24, which is disadvantageous, is greater for shorter wavelength frequencies (i.e., visible light as compared with NIR). Without the greater absorption, due to the optical activity in the visible spectra of bran, the increased surface back-scatter would indicate a greater diffuse reflectance measurement. Thus, the optical activity of bran in the visible light spectra partially offsets the increased surface back-scatter due to the shorter wavelengths of visible light.

In the preferred embodiment, the useful visible light wavelength correlating to flour "ash" range between about 530 nm to 550 nm with the optimum wavelength being about 540 nm. It will be appreciated, however, that other optically active visible light wavelengths, or combinations thereof, may be used in constituent correlation spectroscopic algorithms without departing from the true spirit and nature of the present invention. Moreover, for other analytes a different range of visible light activity would be expected.

In accordance with the present invention and as mentioned above, the correlation spectroscopic algorithm includes another component in combination with the visible light spectra component. It has been found that the addition of an NIR component is particularly useful to offset background interference caused by different protein, starch and moisture constituents also found in flour. Further, as will be described in greater detail below, the NIR component has also been found to be much less susceptible to particle size variations in the differing grain samples. Moreover, the NIR component which is most preferred corresponds to an optically active region of cross over of starch and protein along the NIR spectrum. Accordingly, the present invention, which incorporates both visible light components and NIR component into a single constituent correlation spectroscopy algorithm, is inherently more stable thereby allowing accurate constituent predictions over a wider variety of wheat flour blends.

The NIR wavelengths, in accordance with the present invention, correspond to the optically active range between about 1350 nm to about 1370 nm with the optimum wavelength being about 1360 nm. This range corresponds to what is known as the short-wave near-infrared spectral region which extends between 900 nm to 1400 nm. Thus, the region also falls well below the standard interference filter range between 1445 nm to 2500 nm of the prior quantitative analyzing instruments which determine flour "ash". More importantly, this region for wheat flour is an optically active NIR region which corresponds to a cross-over between the present chromophores of protein and starch which absorb light energy in this region. Absorption in this region, however, is significantly lower than that of the classical 1445 nm to 2500 nm range because of the high reflectance. Accordingly, particle size effects are reduced since a greater percentage of NIR energy is reflected in this optically active region. Generally, since the reflectance of energy is higher, the overall energy penetrating the sample in this optically active region is lower to which the overall absorption is also proportionally lower. Accordingly, this range of NIR wavelengths effectively minimize particle size effects and handle the background interference due to proteins, starch and moisture.

Thus, both the visible light wavelength and the NIR wavelength correspond to optically active regions of flour. The visible wavelength (about 540 nm) corresponding to bran and the NIR wavelength (about 1360 nm) corresponding to the protein/starch spectral crossover. Generally, in the prior instruments, at least one other NIR wavelength is measured as a reflective reference. This reference is normally chosen from an optically inactive portion of the wavelength spectrum and is representative of the overall reflectivity of the particular sample matrix. The present invention eliminates the need for a reference measurement because the optically active measurement in the NIR crossover region effectively handles the aforementioned background interference.

The NIR component also has been determined to be less susceptible to particle size effects, for the reasons discussed above. In practice, it is desirable for the variable particle size difference from sample-to-sample and from sample-to-standards to be minimized. However, uniform particle sizes within the established limits cannot always be attained between milled flour within the same samples as well as between the samples. Fortunately, because of the deeper penetration of the NIR wavelength, it has been found that the diffuse reflectance measurements are less susceptible to particle size effects because the percentage of absorbed NIR light energy, in this region, is decreased.

The present invention preferably is applicable to the constituent determination of wheat flour "ash". Set forth below, is the "ash" correlation spectroscopic algorithm which includes the novel combination of visible light and NIR diffuse reflectance measurements. In accordance with the present invention, the individual wavelength correlation algorithm which corresponds to flour "ash" has been determined to be:

$$\%Bran = a_0 + a_{1360nm}\log(1/R_{1360nm}) + a_{540nm}\log(1/R_{540nm})$$

where, typically, $a_0$ = calibration offset = 2.944;
$a_{1360nm}$ = 1360 nm calibration coefficient = -7.04;
$a_{540nm}$ = 540 nm calibration coefficient = 8.41;
$R_{1360nm} = (I_{1360nm}/I_{1360nm\ Ref})$, i.e., the mesured reflectivity at 1360 nm as compared to the reference intensity at 1360 nm; and
$R_{540nm} = (I_{540nm}/I_{540nm\ Ref})$.

TABLE 2, set forth below, represents the figures corresponding to the predicted flour "ash" set forth in TABLE 1.

TABLE 2

| Sample | Log $(1/R_{1360\ nm})$ | Log $(1/R_{540\ nm})$ | Predicted Ash |
|---|---|---|---|
| #1 | 0.13409 | −0.17109 | 0.430% |
| #2 | 0.13889 | −0.16530 | 0.454% |

TABLE 2-continued

| Sample | Log (1/R$_{1360\,nm}$) | Log (1/R$_{540\,nm}$) | Predicted Ash |
|---|---|---|---|
| #3 | 0.13648 | −0.16743 | 0.461% |
| #4 | 0.13797 | −0.16571 | 0.462% |
| #5 | 0.13728 | −0.16527 | 0.464% |
| #6 | 0.13698 | −0.16499 | 0.474% |
| #7 | 0.12159 | −0.17601 | 0.500% |
| #8 | 0.13995 | −0.15932 | 0.510% |

Thus, as mentioned, the novel concept of incorporating visible light measurements in combination with NIR measurements, in a constituent correlation spectroscopic algorithm, more accurately predicts constituent concentrations over a wider variety of flour samples.

It is apparent from the above-mentioned algorithm that the visible light measurements and the NIR light measurements may be obtained in any sequential order or combination thereof.

Although the preferred algorithm represents an individual wavelength algorithm, it will be appreciated that the algorithm could include derivatives, the difference between the wavelengths, trios of visible and NIR wavelengths or the like without departing from the true spirit and scope of the present invention. Moreover, the algorithms could include individual or combinations of visible light measurements of different wavelengths together with individual or combinations of NIR light measurements of different wavelengths.

While the present invention is most preferably described in connection with an optical analyzer of the type employing interference filters, as shown in FIG. 1, it will be understood that the present invention's novel combination of incorporating visible light measurements together with NIR measurements in a correlation spectroscopic algorithm may work in conjunction with any optical analyzer emitting the specified wavelengths of radiant energy. These include wavelength scanning or monochromatic devices, tilting filter devices or NIREDs to name a few.

Figure 2:
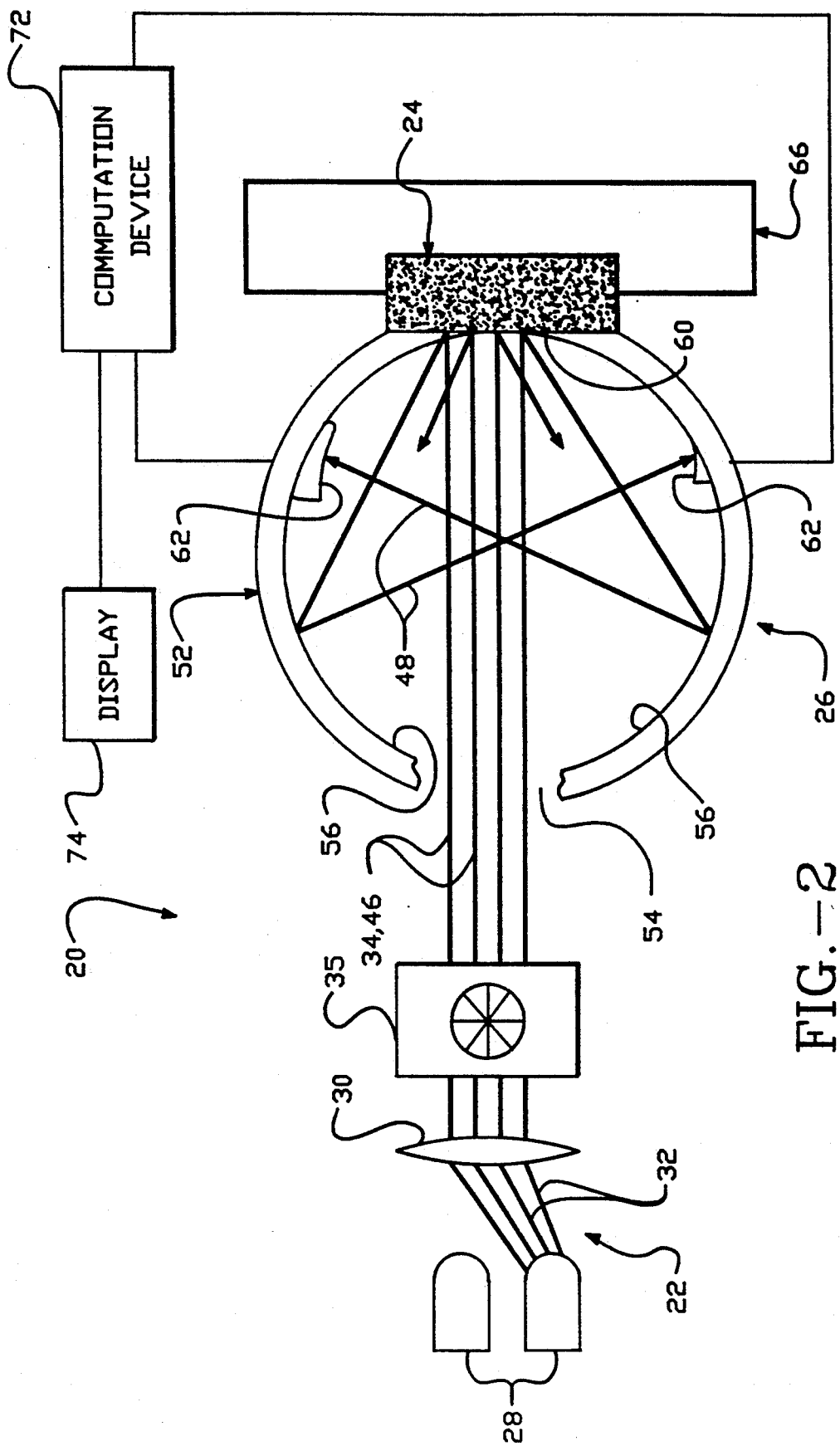
FIG. 2 is a schematical representation of an alternative embodiment of the optical analyzing apparatus of the present invention employing Light Emitting Diodes.

The light emitter assembly 22, as shown in FIG. 1, preferably includes a wide band of wavelengths light source 28 which preferably emits light in both the near-infrared (NIR) spectrum and the visible light spectrum. Accordingly, as discussed above, the preferable NIR range includes wavelengths between about 1350 nm to about 1370 nm while the visible light waVelenqth ranges between about 530 nm to about 550 nm. In the preferred embodiment, a quartz tungsten-halogen light source 28 is desirable because of its wide band of wavelengths. However, it will be appreciated that any light source or two separate light sources emitting radiant energy corresponding to the specified wavelengths may be employed. For example, as shown in FIG. 2, light emitting diodes (LEDs) and near-infrared emitting diodes (NIREDs) may be positioned as narrow wavelength band light emitting sources (i.e., about 540 nm and about 1360 nm) without departing from the true spirit and nature of the present invention.

As best viewed in FIG. 1, in the preferred embodiment, light emitting assembly 22 further includes a collimating lens 30 positioned near light source 28 so that diverging light energy rays 32 diverging from source 28 are refracted substantially parallel to sample 24 which will be discussed below. Collimating lens 30, for example, may comprise a converging lens which is positioned a distance, $f$, from light source 28 which is equivalent to lens' 30 focal length. Accordingly, light source 28 is preferably positioned within lens' 30 focal point wherein the emerging light rays 34 are collimated, as shown in FIG. 1. It is highly desirable for light rays 34 to impinge sample 24 at substantially the same angle to assure measurement reproducibility or accuracy. Therefore, other optical lenses or even collimating mirrors may be employed which refract or reflect the diverging light rays 32 substantially parallel to each other.

As mentioned above, it is preferable that light source 28 be a wide band quartz tungsten-halogen lamp. The remaining undesirable wavelength light energy must be filtered out so that they do not irradiate sample 24. Positioned between light emitting assembly 22 and sample 24 is a filter assembly 36 employing an array of preselected interference filters 38 and 40 which, preferably, correspond to about 540 nm and about 1360 nm, respectively. Filters 38 and 40, preferably transmit a very narrow band of preselected wavelengths, removing the remaining spectra through interference phenomena rather than by absorption or scattering. A best viewed in FIG. 1, filters 38 and 40 are mounted to a rotatable filter turret 42 commonly known in the field. Turret 42 supports filters 38 and 40 and is rotated by stepping motor 44 to sequentially permit irradiation of sample 24 through the corresponding filters 38 and 40.

Positioned between collimating lens 30 and filter assembly 36 is a common light chopper mechanism 35 which is essential for proper measurements. Chopper 35, which can be either mechanical or electronic, oscillates or pulses the radiant energy so that alternating periods of illumination and darkness can be detected. Generally, the illumination period corresponds to the light penetration into sample 24 which is used for the actual optical analysis. The dark measurement, on the other hand, is used to adjust for or calculate out the background electronic interference. Light chopper mechanism 35 is commonly known in the field and is not claimed as part of the present invention.

Accordingly, when a wide wavelength band light source 28 is employed, diverging light rays 32 emitted from light source 28 are collimated (34) by lens 30. The light rays 34 emerge substantially parallel and are pulsed by light chopper 35 wherein they sequentially impinge one of the preselected interference filters 38 or 40. A predetermined wavelength 46, in the visible or NIR spectra, (i.e., about 540 nm or about 1360 nm) is transmitted through filters 38 and 40 wherein it irradiates sample 24 at a predetermined angle. In the preferred form, transmitted light 46 irradiates sample 24 at an angle substantially perpendicular to the surface of sample 24. Thus, the aforementioned algorithm and corresponding coefficients relate to the preselected wavelengths impinging sample 24 perpendicularly thereon. An irradiation at another angle of incident would require a recalibration (i.e., new coefficients). However, it will be appreciated that the novel feature of present invention is the combination of preselected wavelengths of radiant energy in the visible spectra and NIR spectra for a correlation spectroscopic analysis. Therefore, the angle of incident may vary or differ from the preferred angle of incident without departing from the true scope and spirit of the present invention.

After collimated rays 34 have passed through filter assembly 36, the filtered light rays 46 irradiate sample 24. Subsequently, the diffusely reflected light rays 48 need to be collected for measurement. It is noted that any detection device may be employed to detect the diffusely reflected light. In the preferred form, however, sample 24 is often placed in a viewing window of an integrating sphere 52, as viewed in FIGS. 1 and 2. These devices generally provide a beneficial uniform diffuse illumination of sample 24.

Integrating sphere 52 receives filtered light 46 from light source 22 through an entrance port 54 where filter light 46 impinges sample 24 positioned in sample port 60. After irradiation, diffused light 48 emerges from sample 24 back into integrating sphere 52 where the reflected light encounters multiple reflections until it falls upon a detector 62. The diffusely reflecting interior walls 56 of integrating sphere 52 reflect diffused light 48 in multiple reflections so that uniform diffuse illumination is provided over the interior surface of integrating sphere 52. Through this arrangement of suitable optics and strategically positioned detectors 62 within sphere 52, the radiation is collected, input and processed in a computer 72 to obtain the percentage of each constituent in accordance with the predetermined algorithm or formula described above. Subsequently, the consistent percentage figure is conveyed on display 74.

Integrating sphere 52 is commonly known in the field and does not constitute a novel feature of the present invention. Similarly, detectors 62 are commonly known and may be any one of PbSe, PbS, Si, Ge or cooled Ge detectors.

Sample 24 is preferably secured to a stationary sample mounting apparatus 66 positioned near sample port 60. As the collimated filtered light rays 46 enter integrating sphere 52 through entrance port 54, the angle of incident substantially perpendicular to sample 24. Further, stationary sample 24 assures a constant uniform diffuse illumination figure of reflectance or absorbtivity. Alternately, mounting apparatus 66 could include a moving sample holder or moving sample which travels along a predetermined path. Such an apparatus may provide a better overall reflectance or absorbance measurement for a heterogeneous particulate sample.

In an alternative embodiment (not shown), the transmissivity of sample 24 may be measured wherein detectors 62 would be placed on the side opposite the irradiated surface of sample 24. This method measures the transmissivity of the preselected light energy through sample 24 as opposed to its diffuse reflectance. This approach would require a new set of corresponding calibration offsets and coefficients. However, the important feature, in accordance with the present invention, is the novel approach of combining measurements of visible light together with NIR light in a correlation spectroscopic algorithm to determine the constituent concentration.

A method of for optically obtaining quantitative correlation spectroscopy measurements of an analyte concentration in a multiple constituent sample is provided herein. The method comprises the steps of irradiating sample 24 with a predetermined first wavelength (i.e., about 540 nm) of light energy in the visible light spectrum selected to be active in response to the presence of an analyte (bran). Detection of one of a first optical reflectance and transmissivity of sample 24 after it has been irradiated by filtered rays 46. The sample must also be irradiated with a predetermined second wavelength (i.e., about 1360 nm) of light energy in the near-infrared (NIR) spectrum selected to be active in response to the presence of at least one of the remaining constituents (protein and starch) in sample 24. Further, detection of one of a second optical reflectance and transmissivity of sample 24 after irradiation at the second wavelength must also occur. With these measurements, a value of the concentration through correlation spectroscopy algorithms is predicted employing the first and the second detected one of reflectance and transmissivity of sample 24.

While the invention has been described in connection with what is presently considered to be the most practical and preferred embodiments, it is to be understood that the invention is not limited to the disclosed embodiment but, on the contrary, is intended to cover various modifications and equivalent arrangements included within the spirit and scope of the appended claims.

Therefore, persons of ordinary skill in this field are to understand that all such equivalent structures are to be included within the scope of the following claims.

What is claimed is:

1. An optical analyzing apparatus for obtaining quantitative compositional correlation spectroscopy measurements of an analyte concentration in a multiple constituent flour product sample, said optical analyzing apparatus comprising:

light emitter means formed for irradiating said sample with a predetermined first wavelength of light energy in the visible light spectrum in the range between about 530 nm to about 550 nm selected to be active in response to the presence of said analyte, and a predetermined second wavelength of light energy in the near-infrared (NIR) spectrum in the range between about 1350 nm to about 1370 nm selected to be active in response to the presence of at least one of the remaining constituents in the sample; and detector means positioned to detect one of optical reflectance and transmissivity of the ample after said irradiation at said first wavelength and said second wavelength, whereby the detected one of reflectance and transmissivity can be used in a compositional correlation spectroscopy algorithm to obtain a value of said concentration.

2. The optical analyzing apparatus as defined in claim 1 further including:

computation means coupled to said detector means for calculating said value from the detected one of reflectance and transmissivity of the sample using said algorithm.

3. The optical analyzing apparatus as defined in claim 2 wherein, said computation means includes means for determining the value of said concentration in accordance with the following compositional correlation spectroscopy algorithm:

$$\%_{Analyte} = a_0 + a_1 \log(1/R_1) + a_2 \log(1/R_2)$$

in which the constants $a_0$, $a_1$ and $a_2$ are constants having predetermined values, $R_1$ is the reflectance from the sample due to said predetermined visible light wavelength, and $R_2$ is the reflectance from the sample due to said predetermined NIR light wavelength.

4. The optical analyzing apparatus as defined in claim 1 wherein, said light emitter means comprising a wide band wavelength light, first filter means positioned between said light and said sample and permitting irradiation of said sample by said first wavelength of light energy, and second filter means positioned between said light and said sample and permitting irradiation of said sample by said second wavelength of light energy.

5. The optical analyzing apparatus as defined in claim 4 wherein,
said light is a quartz tungsten-halogen light source.

6. The optical analyzing apparatus as defined in claim 4 wherein,
said first filter means and said second filter means are preselected interference filters.

7. The optical analyzing apparatus as defined in claim 4 wherein,
said first and second filter means are fixed to a rotatable turret means operable to sequentially rotate said first and second filters between said light and said sample.

8. The optical analyzing apparatus as defined in claim 1 wherein,
said light emitter means comprise a light emitting diode (LED) emitting light corresponding to said first wavelength of light energy, and a NIR emitting diode (NIRED) emitting light corresponding to said second wavelength of light energy.

9. The optical analyzing apparatus as defined in claim 1 wherein,
said light emitter means sequentially irradiates said sample with said first wavelength of light energy and with said second wavelength of light energy.

10. The optical analyzing apparatus as defined in claim 1 wherein,
said flour product sample is provided by wheat flour and said analyte is any one of bran and cellulose.

11. The optical analyzing apparatus as defined in claim 1 wherein,
said first wavelength of visible light energy is about 540 nm.

12. The optical analyzing apparatus as defined in claim 1 wherein,
said first wavelength of visible light energy is about 540 nm, and said second wavelength of NIR light energy is about 1360 nm.

13. The optical analyzing apparatus as defined in claim 1 wherein,
said second wavelength of NIR light energy is about 1360 nm.

14. The optical analyzing apparatus as defined in claim 1 wherein,
said sample is positioned for irradiation in an integrating sphere and said detector means are strategically located therein.

15. An optical analyzing apparatus for obtaining a compositional quantitative measurement of an analyte concentration in a multiple constituent flour product sample, said optical analyzing apparatus comprising:
light emitter means formed for irradiating the sample with light energy;
first filter means positioned between said light emitter means and said sample, and permitting irradiation of said sample by predetermining wavelength of light energy in the visible light spectrum in the range between about 530 nm to about 550 nm selected to be active in response to the presence of said analyte;
second filter means positioned between said light emitter means and said sample, and permitting irradiation of said sample by a predetermined wavelength of light energy in the near-infrared (NIR) spectrum in the range between about 1350 nm to about 1370 nm selected to be active in response to the presence of at least one of the remaining constituents in the sample;
detector means positioned to detect one of optical reflectance and transmissivity of the sample after said irradiation at said wavelength in the NIR spectrum and said wavelength in the visible spectrum; and
computation means coupled to said detector means for calculating said compositional quantitative measurement from the detected one of reflectance and transmissivity of the sample.

16. The optical analyzing apparatus as defined in claim 15 wherein,
said first filter means and said second filter means are preselected interference filters.

17. The optical analyzing apparatus as defined in claim 15 wherein,
said irradiation of said sample with said first wavelength of light energy and with said second wavelength of light energy is sequential.

18. The optical analyzing apparatus as defined in claim 15 wherein,
said product sample is provided by wheat flour.

19. The optical analyzing apparatus as defined in claim 18 wherein,
said analyte is any one of bran and cellulose.

20. The optical analyzing apparatus as defined in claim 15 wherein,
said first wavelength of visible light energy is about 540 nm.

21. The optical analyzing apparatus as defined in claim 20 wherein,
said second wavelength of NIR light energy is about 1360 nm.

22. In an optical analyzing apparatus for obtaining quantitative compositional correlation spectroscopy measurements of flour "ash" concentration in a multiple constituent wheat flour sample, said optical analyzing apparatus including light emitter means formed for irradiating said sample with light energy and detector means positioned to detect one of optical reflectance and transmissivity of the sample after said irradiation, said detected one of reflectance and transmissivity can be used in a compositional correlation spectroscopy algorithm to obtain a value of said concentration, wherein the improvement comprises:
said light emitter means irradiating said sample with a predetermined first wavelength of light energy in the visible light spectrum in the range between about 530 nm to about 550 nm selected to be active in response to the presence of said flour "ash", and a predetermined second wavelength of light energy in the near-infrared (NIR) spectrum in the range between about 1350 nm to about 1370 nm selected to be active in response to the presence of at least one of the remaining constituents in the sample.

23. The optical analyzing apparatus as defined in claim 22 wherein,
said flour "ash" includes any one of bran and cellulose.

24. The optical analyzing apparatus as defined in claim 22 wherein,
said first wavelength of visible light energy is about 540 nm.

25. The optical analyzing apparatus as defined in claim 22 wherein, said first wavelength of visible light energy is about 540 nm, and said second wavelength of NIR light energy is about 1360 nm.

26. The optical analyzing apparatus as defined in claim 22 wherein,
said second wavelength of NIR light energy is about 1360 nm.

27. A method for optically obtaining quantitative compositional correlation spectroscopy measurements of an anlayte concentration in a multiple constituent flour product sample, said method comprising the steps of:
irradiating said flour product sample with a predetermined first wavelength of light energy in the visible light spectrum selected to be active in response to the presence of said analyte;
detecting one of a first optical reflectance and a first optical transmissivity of the flour product sample after said irradiation at said first wavelength;
irradiating said flour product sample with a predetermined second wavelength of light energy in the near-infrared (NIR) spectrum selected to be active in response to the presence of at least one of the remaining constituents in the flour product sample;
detecting one of a second optical reflectance and a second optical transmissivity of the flour product sample after said irradiation at said second wavelength;
calculating a value of said concentration of said analyte using a compositional correlation spectroscopy algorithm from said first and said second detected one of reflectance and transmissivity of the flour product sample.

28. The method as defined in claim 27 wherein,
said step of irradiating said sample with a first wavelength of light energy is accomplished by irradiating said sample with visible light energy having a wavelength in the range of about 530 nm to about 550 nm.

29. The method as defined in claim 28 wherein, said step of irradiating said sample with a second wavelength of light energy is accomplished by irradiating said sample with NIR energy having a wavelength in the range of about 1350 nm to about 1370 nm.

30. The method as defined in claim 29 wherein,
said step of irradiating said sample with a first wavelength of light energy is accomplished by irradiating said sample with visible light energy having a wavelength of about 540 nm; and
said step of irradiating said sample with a second wavelength of light energy is accomplished by irradiating said sample with NIR light energy having a wavelength of about 1360 nm.

* * * * *